United States Patent
Alexandre et al.

(10) Patent No.: US 6,911,015 B2
(45) Date of Patent: Jun. 28, 2005

(54) NEEDLELESS SYRINGE FUNCTIONING BY SHOCK-TUBE EFFECT, WITH PRIOR LATERAL RETENTION OF THE ACTIVE PRINCIPLE

(75) Inventors: Patrick Alexandre, Gray (FR); Georges Baud, La Crau (FR); Guy Delannoy, Saint Medard en Jalles (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 486 days.

(21) Appl. No.: 10/148,340

(22) PCT Filed: Dec. 18, 2000

(86) PCT No.: PCT/FR00/03567

§ 371 (c)(1),
(2), (4) Date: May 29, 2002

(87) PCT Pub. No.: WO01/47585

PCT Pub. Date: Jul. 5, 2001

(65) Prior Publication Data

US 2002/0183689 A1 Dec. 5, 2002

(30) Foreign Application Priority Data

Dec. 27, 1999 (FR) .......................................... 99 16536

(51) Int. Cl.[7] .......................... A61M 5/30; A61M 37/00
(52) U.S. Cl. .............................. 604/69; 604/68; 604/140
(58) Field of Search ........................... 604/68, 69, 140, 604/141

(56) References Cited

U.S. PATENT DOCUMENTS

| | | | |
|---|---|---|---|
| 3,763,859 A | 10/1973 | Yanof et al. | |
| 3,788,315 A | 1/1974 | Laurens | |
| 4,089,334 A | 5/1978 | Schwebel et al. | |
| 4,338,980 A | * 7/1982 | Schwebel et al. | ............. 141/18 |
| 5,478,744 A | 12/1995 | Sanford et al. | |
| 5,865,796 A | 2/1999 | McCabe | |

FOREIGN PATENT DOCUMENTS

| | | | | |
|---|---|---|---|---|
| GB | WO 94/24263 | * 4/1984 | ............ C12M/3/00 |
| WO | WO 94/24263 | 10/1994 | |
| WO | WO 99/01169 | 1/1999 | |

* cited by examiner

Primary Examiner—Brian L. Casler
Assistant Examiner—Lina R Kontos
(74) Attorney, Agent, or Firm—Oliff & Berridge, PLC

(57) ABSTRACT

The invention concerns a needleless syringe (1) comprising a trigger, a gas generator (2) prolonged by a gas expansion chamber (3), a system for retaining particles and an ejection tube (4). The invention is characterised in that the particles are housed outside the ejection tube conduit (4) and the gases cause the particles to reach inside said tube (4) by displacing a plunger (13), prior to speeding them up by wave shock inside the tube (4).

16 Claims, 4 Drawing Sheets

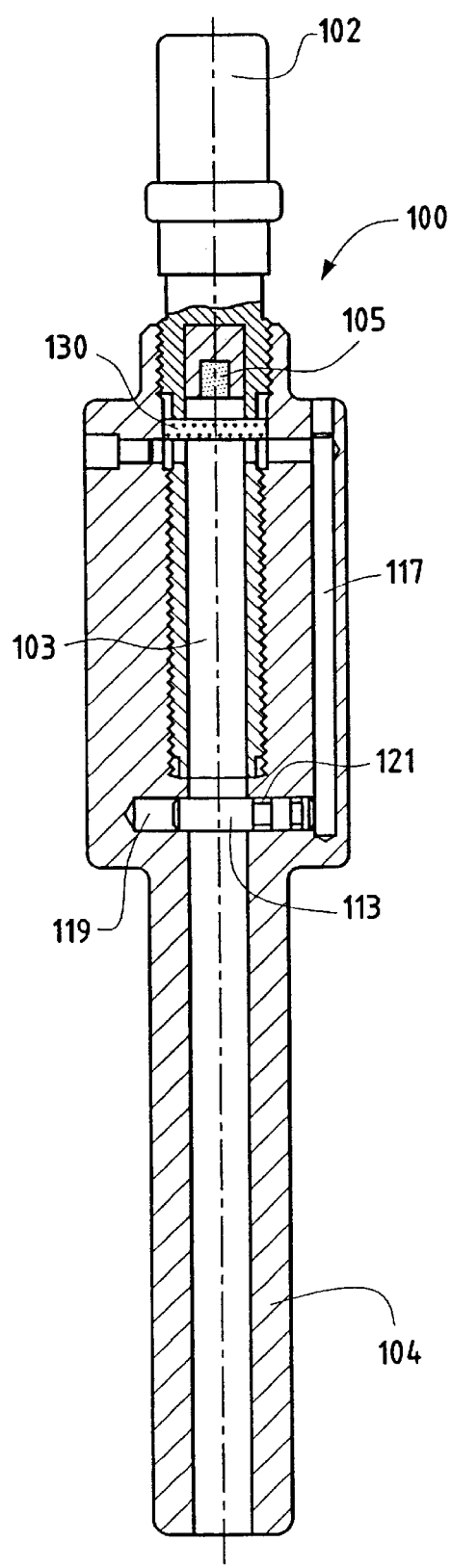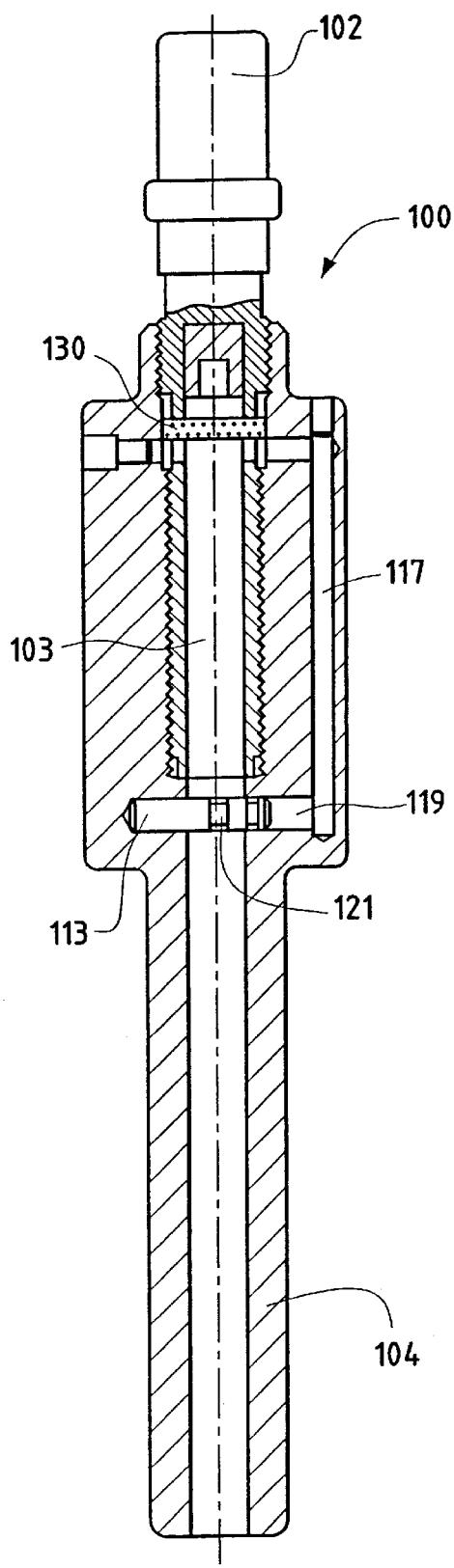
FIG.5
FIG.6

NEEDLELESS SYRINGE FUNCTIONING BY SHOCK-TUBE EFFECT, WITH PRIOR LATERAL RETENTION OF THE ACTIVE PRINCIPLE

The technical field of the invention is that of needleless syringes used for intradermal, subcutaneous or intramuscular injection of various active principles in pulverulent form for therapeutic use in human or veterinary medicine.

More specifically, the invention relates to a needleless syringe using a gas generator which is intended to create a pressure wave for ejecting the particles of active principle. A burstable protective seal, placed on the pathway of the gases, makes it possible to obtain the threshold pressure level permitting ejection of the particles at a sufficiently high speed. This is because the sudden release of the gases creates a shock wave in the syringe and it is this wave which will carry and accelerate the particles in order to expel them. The specificity of the invention lies in the fact that the particles initially isolated from the main ejection circuit of the syringe are first conveyed into the pathway of the gases just before being blown by the shock wave onto the patient's skin.

The needleless syringes which function by generation of a shock for entraining the solid particles of active principle already exist and have been the subject of several patents. Mention may be made, in particular, of patent WO 94/24263 which describes a needleless syringe functioning by release of a reserve of compressed gas in order to entrain the solid particles of active principle. In said patent, one of the main characteristics is that the particles are maintained permanently on the pathway of the gases, between two burstable membranes. At no point is it suggested to store the particles outside the main circuit of ejection of the particles. Mention must also be made of patent WO 99/01169 which refers to a needleless syringe functioning with a capsule intended to contain the active principle and made up of two elements coupled together, one of which is movable. Under the effect of the arrival of the compressed gases, the movable element of the capsule is displaced, thereby creating a passage through said capsule. The active principle is then entrained in this passage by the compressed gases and is subsequently blown toward the patient's skin. In said patent, the active principle is still maintained in the pathway of the gases, and the passage permitting the escape of the active principle is created by the displacement, along the axis of the syringe, of one of the constituent elements of the system for retention of the particles.

There are also devices, such as that described in patent U.S. Pat. No. 5,478,744, for example, with which it is possible to bombard cell cultures with inert or biologically active particles, and whose operating principle is based on the release of a compressed gas into a tube which can be supplied with the particles from the side. It must be noted, however, that these are laboratory devices and, although they are effective, they are heavy and cumbersome and their characteristics are not directly transferable to a lightweight object of small size such as a needleless syringe.

The needleless syringe according to the invention is able to eject solid particles of active principle under the effect of a shock produced by a compressed gas, and permitting the following two steps: first, the particles which are situated in seats outside the ejection tube are released into said tube, then the shock wave passes through the tube, entraining with it the particles already in motion. Thus, the needleless syringe according to the invention has a system for entraining the particles which is small and effective and avoids permanently maintaining said particles in the pathway of the gases. In this way, the particles of active principle are isolated and completely inaccessible, thereby reinforcing the reliability of the syringe. Moreover, since the particles are blown freely into the ejection tube prior to the passage of the shock wave, there is zero risk of ejecting undesirable fragments originating, for example, from membranes for retention of the particles of active principle.

The subject of the present invention is a needleless syringe comprising a trigger, a gas generator continued by a gas expansion chamber, a system for retention of the particles, and an ejection tube, characterized in that the particles are housed outside the conduit of the ejection tube and the gases bring about the entry of the particles into said tube by displacement of a piston, then their acceleration in the tube in order for them to be ejected. Preferably, the needleless syringe according to the invention is adapted in particular for injection of active principle in pulverulent form or in the form of dry powder. The main characteristic of the needleless syringe according to the invention is that of permitting entry of the particles of active principle into the ejection tube just before the shock generated by the gases in said tube carries them off. Such a syringe displays its full efficacy when the time interval between the moment the particles are released into the ejection tube and the moment the shock wave interacts with them is short, that is to say of the order of a millisecond or a few milliseconds. The reason for this is that, at the moment when they are blown out, the particles must still be in the phase of dispersion in the syringe, in the form of a more or less homogeneous "cloud", without their having had the time to reconstitute by the simple effect of gravity. This condition is necessary to ensure a uniform injection without inadvertently favoring specific zones of impact on the skin. The gas generator is preferably a pyrotechnic generator comprising a pyrotechnic charge and an initiation device. According to a preferred embodiment of the invention, the initiation device comprises a percussion device and a primer currently used in the pyrotechnics industry. However, it is also possible to initiate the pyrotechnic charge by other means, and in particular those involving either a piezoelectric crystal or a roughened area or even a battery. The needleless syringe according to the invention can also function with a gas generator formed by a reserve of compressed gas. The trigger is advantageously situated at one of the ends of the syringe in the form of a push button in order to make it easier to grip and operate.

According to a first preferred embodiment of the invention, the particles are situated in at least one fixed seat outside the conduit of the tube, each seat being obturated by the piston positioned in said tube, said piston being displaceable, under the effect of the gases, in order to open each seat and release the particles into the tube. A propulsion device advantageously allows the particles released by the piston to be thrust into the tube from their seat. The reason for this is that, because the objective is to inject the greatest quantity of active principle present in the syringe, it is indispensable to ensure that all the seats are emptied completely so that all the particles are in position to be ejected. According to a preferred embodiment of the invention, the propulsion device is established by conveying gas via at least one duct connecting that zone of the chamber situated near the gas generator to the seats for the particles, and there will preferably be as many ducts as there are seats for the particles. In this way, the device for propulsion of the particles is based on a pre-existing source of energy and does not entail any increased volume due to an additional separate and independent device. The particles are advantageously housed in the end part of each duct, against the piston. More precisely, the particles are housed in a space which is delimited, on the one hand, by the piston, and, on the other hand, by a thin transverse film situated in the duct. This thin film can be formed, for example, by a burstable membrane of very small thickness which is unable to withstand a pressure greater than 10 bar, or alternatively a porous membrane.

According to another embodiment of the invention, the particles are blocked in their seat, between the piston and a prestressed spring, in such a way that, when the piston no longer obturates the seats, each spring will relax and propel the particles into the tube. The piston is preferably formed by a hollow cylindrical body whose side wall has at least one opening. There are preferably as many openings as there are seats for the particles, and said seats are distributed uniformly about the tube, being in alignment and spaced apart at regular intervals. The tube advantageously has a device for arresting and positioning the piston, situated between said piston and that end of the tube through which the particles are ejected. The limit stop device is preferably designed to arrest the piston, moved by the gases, in a position in which each opening on its side wall corresponds with each seat for the particles. Thus, under the effect of the pressure generated by the gases, the piston is displaced and locks in a position allowing the particles to invade a portion of the tube. The piston preferably has a transverse protective seal and is positioned in the tube in such a way that the protective seal is situated upstream of the openings, and said protective seal is calibrated so as to yield at a threshold pressure reached by the gases when the piston is arrested by the limit stop device. Chronologically, the functioning of a syringe according to this preferred embodiment has two distinct phases: the first during which the piston is displaced and locks against the limit stop device, thus making it possible to release the particles into the tube; and the second phase which occurs just after the first one and during which the pressure of the gases in the space between the gas generator and the protective seal increases until it reaches a threshold value resulting in perforation of said protective seal. The sudden release of the compressed gases as a result of the rupturing of the protective seal creates a pressure wave that can be likened to that of a shock. The wave thus emitted into the ejection tube sets in motion the particles in the form of a cloud and these particles are ejected at high speed. The limit stop device is advantageously formed by a crown fixed to the inside of the tube. This is because the component constituting the limit stop device must serve as a stop for the piston but must not prevent the particles from passing. This component must therefore be of an openwork configuration and can also, for example, assume the form of a transverse grille.

According to a second preferred embodiment of the invention, the tube has a transverse channel in which is housed the piston which has a solid part and a hollow part containing the particles, and said piston, which is housed in the transverse channel so as to initially obturate the tube with its solid part, can be displaced along the transverse channel, by virtue of a thrust device, until its hollow part is positioned in the continuation of the tube. The thrust device is preferably established by conveying gas via a duct connecting that zone of the chamber situated near the gas generator to the transverse channel. In the same way as has been described for the first preferred embodiment of the invention, the thrust device for the piston, and hence for the particles, is based on a preexisting source of energy, making it possible to save space while at the same time being particularly effective. The transverse channel advantageously has a locking means for holding the piston in a position in which its hollow part is situated in continuity with the tube. Thus, in a first step, under the effect of the gases, the piston is displaced so as to release the particles of active principle into the tube and free them. Preferably, the hollow part of the piston containing the particles is initially closed by the wall of the transverse channel. The hollow part of the piston advantageously has a protective seal so that, on being displaced, the piston opens its hollow part in such a way as to bring the particles into the tube, and the protective seal is intended to yield at above a threshold pressure in order to expel the particles. The protective seal is advantageously placed upstream of the particles in relation to the direction of propagation of the gases in the syringe, in such a way as to burst and create a shock wave just before interacting with the particles which are already in motion. In this way, when the piston is displaced and is locked by the locking means in the transverse channel, the syringe has, in succession and in continuity, the gas generator, an expansion chamber for the combustion gases which is delimited by the protective seal of the piston, the protective seal, the freed particles of active principle, and, finally, the tube for ejection of said particles. Once the threshold pressure has been reached by the gases, the protective seal yields, and the shock thus created abruptly accelerates the freed particles situated downstream of said protective seal in relation to the movement of the gases, and ejects them toward the patient's skin. According to another embodiment of the invention, the piston can also be in the form of an initially tight subassembly in which, in particular, the hollow part is closed by way of two movable tongues. For this configuration, the displacement of the piston in the transverse channel allows one of the two tongues to be drawn back in order first to release the particles into the tube, the other tongue acting as a protective seal. The tongue can also be torn, the main objective being to create an opening to permit deconfinement and release before the acceleration of the particles in the tube by the shock wave. According to another embodiment of the invention, the thrust device is formed by a spring. The spring is advantageously prestressed between the piston, which transports particles and is locked against a movable limit stop, and one of the ends of the transverse channel. Preferably, the actuation of the trigger results, on the one hand, in the lifting of the movable limit stop, thereby permitting displacement of the piston under the effect of the spring which loses its tension, and, on the other hand, the activation of the gas generator in order to bring the gases into the ejection tube. These two actions are separate from one another and must take place at a very short time interval in order to ensure homogeneous injection of the deconfined particles.

The needleless syringes according to the invention benefit from the advantages associated with functioning by means of shock, in particular in terms of the speed of ejection of the particles, while at the same time ensuring reliable maintenance of the particles in storage mode.

Moreover, the wide variability of the pyrotechnic compositions which can constitute the energy source of the syringes permits great flexibility of use, making it possible to adjust the parameters of the "motor" of the syringe to the particular case to be treated.

Finally, when the particles are thrust into the ejection tube by diversion of the combustion gases, and when the gas generator comprises a very small pyrotechnic charge, the needleless syringe is equipped with an operating mechanism which is extremely effective but small, giving it a particularly striking functional character.

Several preferred embodiments of the invention are described in detail below with reference to FIGS. 1 to 7.

FIG. 5 is a partial view, in longitudinal cross section, of a needleless syringe according to the invention, the particles being housed in a piston situated in a transverse channel, and the syringe having not yet been used.

FIG. 6 shows the syringe from FIG. 5, but after it has been used.

Figure 1:
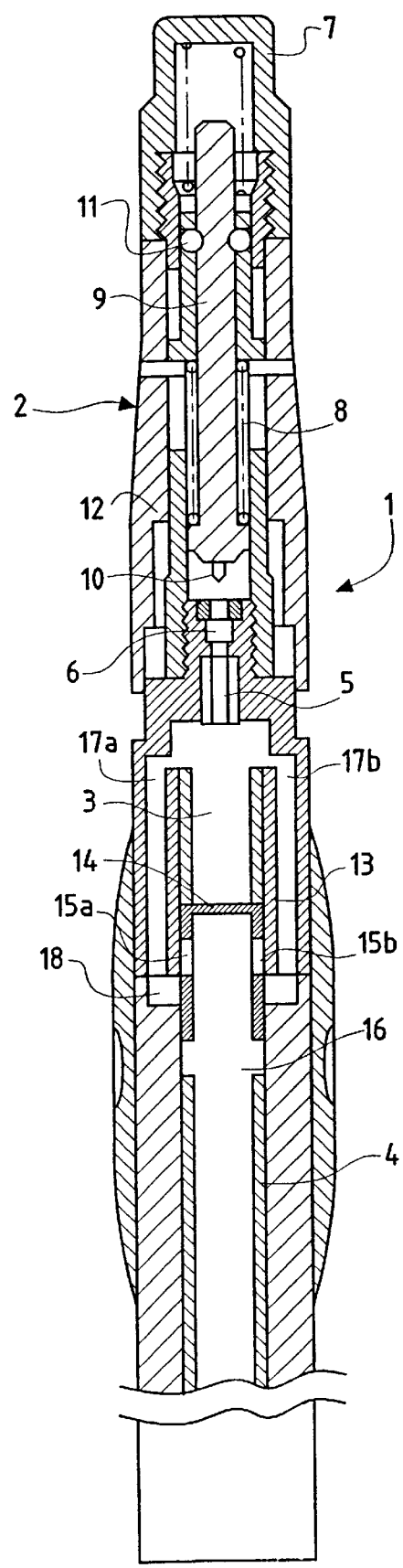
FIG. 1 is a diagram showing a longitudinal cross section through a needleless syringe according to the invention, the particles being housed in at least two fixed seats situated outside the conduit of the ejection tube.

Referring to FIG. 1, a needleless syringe 1 according to the first preferred embodiment of the invention comprises, in succession, a pyrotechnic gas generator 2, an expansion chamber 3, a system for retention of the particles, and a tube 4 used for ejection of said particles and intended to bear against the skin of the patient who is to be treated.

The pyrotechnic gas generator 2 comprises an initiation device for a pyrotechnic charge 5 involving a percussion device and a primer 6. The percussion device, which is triggered by a push button 7, comprises a spring 8 and an elongate weight 9 equipped with a striker 10. The weight 9 is blocked by at least one immobilizing ball 11 wedged between said weight 9 and a hollow cylindrical body 12 in which said weight 9 can be displaced. The primer 6 and the pyrotechnic charge 5, of substantially cylindrical shape, are accommodated in the hollow cylindrical body 12 downstream of the weight 9. The pyrotechnic charge 5, which is accommodated in the hollow body 12, has a plane circular face opening onto a free space of the syringe constituting the expansion chamber 3 for the gases which will issue from the combustion of the pyrotechnic charge 5.

Figure 2:
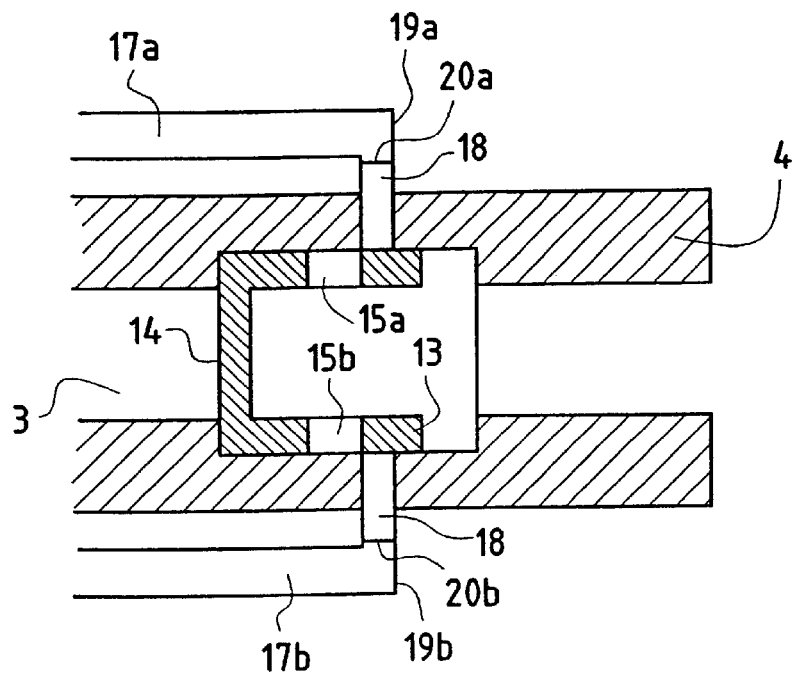
FIG. 2 is a diagram showing a longitudinal cross section through the system for retention of the particles in the syringe in FIG. 1.

Referring to FIG. 2, this chamber 3, of substantially cylindrical shape, is delimited, at its end remote from that formed by the pyrotechnic charge 5, by a piston 13 which is made up of a hollow cylindrical body, in cross section, one of whose ends is free and the other of which is closed by a protective seal 14 which can burst beyond a threshold pressure in said chamber 3.

More specifically, it is the plane protective seal 14 of the piston 13 which delimits the length of the chamber 3. The hollow cylindrical body of said piston 13 has two diametrically opposite openings 15a, 15b.

The piston 13 is positioned in the syringe 1 in such a way that its free end is situated toward the ejection tube 4 and the protective seal 14 is placed upstream of said free end with respect to the direction of propagation of the gases issuing from the combustion of the pyrotechnic charge 5. The outer lateral wall of the piston 13 is in contact with the inner lateral wall of a channel 16 which continues the chamber 3, said channel 16 itself being continued by the conduit of the ejection tube 4. The chamber 3, the intermediate channel 16 and the ejection tube 4 are of cylindrical shape, said chamber 3 and said conduit of the tube 4 having the same diameter, and the intermediate channel 16 having a greater diameter. These three elements, which are in continuity with one another, are delimited by internal shoulders marking their difference in diameter. Two ducts 17a, 17b situated in the thickness of the syringe 1 and parallel to the axis of the chamber 3 each connect the chamber 3 to the intermediate channel 16. More precisely, each of the ducts 17a, 17b starts in the chamber 3, in a zone very close to the pyrotechnic charge 5, and ends approximately in the median part of the intermediate channel 16. The piston 13, which is situated in the channel 16, is blocked against the internal shoulder marking the boundary between the chamber 3 and said intermediate channel 16, and its hollow cylindrical body obturates the end of the two ducts 17a, 17b opening into the channel 16 such that the two openings 15a, 15b are situated between the protective seal 14 and the part of the hollow cylindrical body of the piston 13 obturating the two ducts 17a, 17b. These two ducts 17a, 17b, which are parallel to the axis of the chamber 3, each have an elbow allowing them to include a small end segment 19a, 19b opening into the channel 16, perpendicular to its axis. The active principle, which is pulverulent or in the form of a dry powder, occupies each of the two small segments 19a, 19b of the ducts 17a, 17b, in a space 18 delimited, on the one hand, by the lateral wall of the piston 13, and, on the other hand, by a porous membrane 20a, 20b arranged transversely in each duct 17a, 17b.

The tube 4 for ejection of the particles of active principle has the same diameter as that of the chamber 3 and can advantageously end in a shock-absorbing rim in order to facilitate the contact of the syringe 1 on the patient's skin.

This first preferred embodiment of the invention functions in the following way.

The user positions the syringe 1 in such a way that the end of the ejection tube 4 bears against the skin of the patient who is to be treated.

Pressure on the push button 7 means, on the one hand, that the hollow cylindrical body 12 is displaced until its widened part is in line with the immobilizing ball 11, and, on the other hand, that the spring 8 is compressed. The ball 11 leaves its seat, thereby freeing the weight 9 which, subjected to the action of the spring 8 which releases, is abruptly accelerated toward the primer 6, with the striker 10 leading. The reaction of the primer 6 results in the firing of the pyrotechnic charge 5 which emits gases which simultaneously invade the expansion chamber 3 and the two ducts 17a, 17b. When the pressure in the chamber 3 reaches a threshold level, the piston 13 is displaced linearly in the intermediate channel 16 until it comes into abutment against the internal shoulder marking the boundary between said channel 16 and the ejection tube 4. This final position of the piston 13 corresponds to its two openings 15a, 15b coming into line with the small end segment 19a, 19bof each duct 17a, 17b.

Before the piston 13 comes into abutment, the active principle is confined and begins to spread into the ejection tube 4 by virtue in particular of the thrust from the gases situated in the ducts 17a, 17b. Once the piston 13 has come into abutment, the whole of the active principle is in motion in the ejection tube 4 while the pressure in the chamber 3 continues to increase very rapidly. When the pressure reaches a threshold value, the protective seal 14 eventually yields, thereby releasing a shock wave which reaches, picks up and accelerates the particles still in the form of a diffuse cloud. The release of these particles into the tube 4 and the rupture of the protective seal 14 must take place over a very short interval, of the order of a millisecond or of a few milliseconds, in order to ensure that the particles have not had time to regroup.

Figure 3:
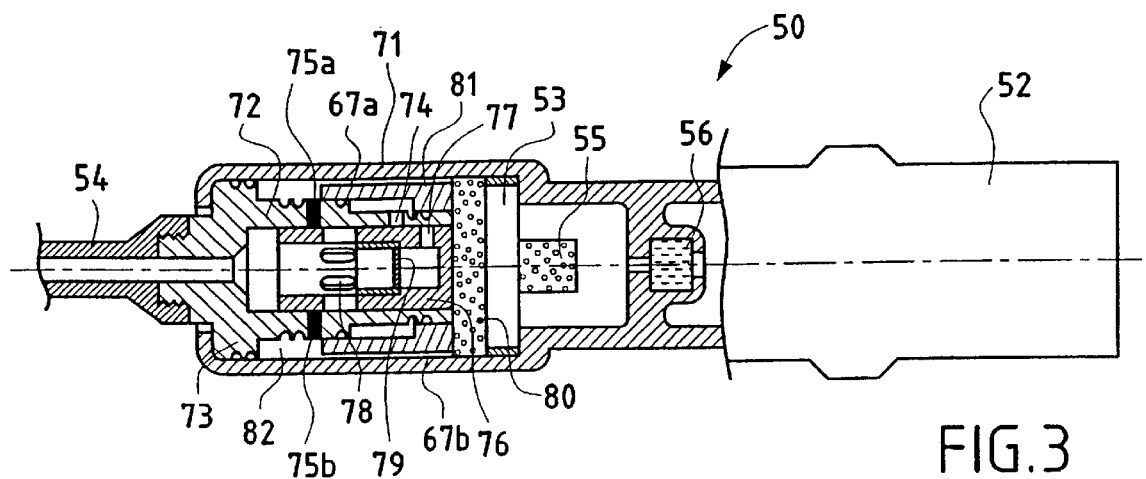
FIG. 3 is a diagram showing a longitudinal cross section through a preferred embodiment of the needleless syringe according to the invention, the syringe having not yet been used, and the particles being housed in six fixed seats situated outside the ejection tube.
Figure 4:
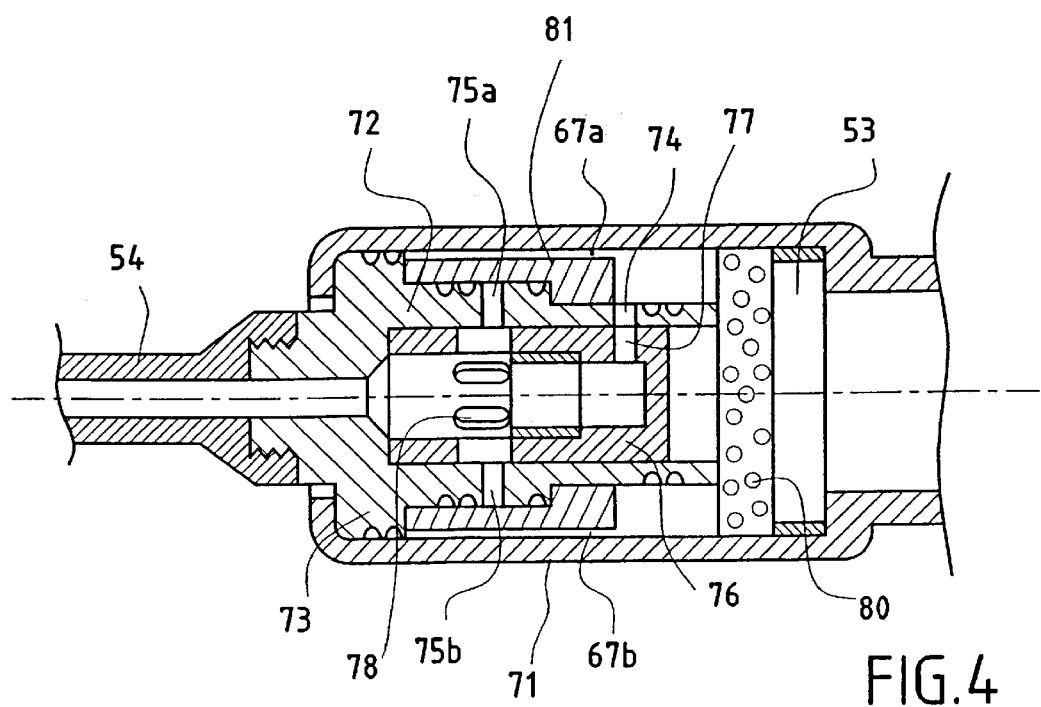
FIG. 4 is an enlarged view, in longitudinal cross section, of the syringe in FIG. 3 after use.

Referring to FIGS. 3 and 4, a needleless syringe 50 according to another version of the first embodiment of the invention also comprises a pyrotechnic gas generator 52, an expansion chamber 53, a system for retention of the particles, and a tube 54 for ejection of said particles which is intended to bear against the skin of the patient who is to be treated.

The pyrotechnic gas generator 52 comprises an initiation device 55 for a pyrotechnic charge, involving a percussion device and a primer 56. The characteristics of the percussion device (not shown in FIGS. 3 and 4) are identical to those of the percussion device described for the first embodiment of the invention. The pyrotechnic generator 52, one end of which is delimited by the pyrotechnic charge 55, is continued, at said end, by a hollow cylindrical body 71, which is itself continued by the ejection tube 54. The end of said body 71, situated toward the tube 54, has been turned inward to form a right angle, so that it has a central opening of smaller diameter than that of the body 71. In the continuity of the gas generator 52, the hollow body 71 has, in succession, the chamber 53 of substantially cylindrical shape, a transverse filter 80 fixed to said body 71, and the system for retention of the particles of active principle comprising a substantially cylindrical, hollow fixed component 72 which is immobilized between the filter 80 and the turned-in end' of the hollow body 71. The hollow component 72 has a cylindrical central channel of constant diameter which is continued by a convergent part which opens into the ejection tube 54. The free end of said cylindrical central channel of constant diameter is obturated by the filter 80. The external diameter of said component 72 is smaller than the internal diameter of the hollow body 71, so that a space is left between these two elements. Said hollow component 72 has a widened cylindrical base 73, the outer wall of which is in contact with the inner wall of the hollow body 71, said base 73 being situated in abutment against the turned-in end of said body 71. This fixed component 72 has, in its upstream part, a series of first orifices 74 (only one of which is shown) passing through its lateral wall, and, in its part situated farther downstream, six other orifices 75a, 75b which are diametrically opposed and also run through its lateral wall, these diametrically opposite orifices 75a, 75b being intended to accommodate the solid particles of active principle. The central channel of the fixed component 72 houses a piston 76 represented by a hollow cylindrical body, the outer lateral wall of which is in contact with the inner lateral wall of said channel, and having a closed end in contact with the filter 80 and another open end. In an upstream zone, the lateral wall of the piston 76 is traversed by a series of orifices 77 (only one of which is shown), and in a downstream zone said piston 76 has six openings 78 also running through its lateral wall, said openings 78 being aligned with one another and being uniformly distributed on the periphery of said piston 76. The length of the piston 76 is less than the length of the central channel of the component 72, and the piston 76 is placed in said channel such that its closed end is in contact with the surface of the filter 80. The internal channel of the piston 76 has, in continuity with one another, an upstream part and a downstream part separated by a transverse protective seal 79 which has lines of weakening making it possible to define a star shape, said protective seal 79 being integral with said piston 76. The orifices 77 open into the upstream part of the channel of the piston 76, and the openings 78 open into the downstream part of said channel. The space situated between the hollow cylindrical body 71 of the syringe 50 and the fixed hollow cylindrical component 72 is partially occupied by a cylindrical crown-shaped component 81, the length of which is less than the length of said space delimited by the widened base 73 of said hollow component 72 and the filter 80, and having at its periphery at least two longitudinal rectilinear grooves parallel to one another and to its axis of revolution, in such a way as to constitute two ducts 67a, 67b between the outer lateral wall of said cylindrical component 81 and the inner lateral wall of the hollow cylindrical body 71. Said crown-shaped component 81 is positioned against the filter 80, permitting the existence of a free space 82 delimited, on the one hand, by the outer lateral wall of the fixed hollow component 72 and the inner lateral wall of the hollow cylindrical body 71, and, on the other hand, by the widened base 73 of said hollow component 72 and one of the ends of the crown-shaped component 81. The various components described above are arranged in relation to one another in such a way that the orifices 75a, 75b, intended to receive the particles of active principle, are on the one hand obturated by the lateral wall of the piston 76 situated downstream of the openings 78, and, on the other hand, open into the free space 82 situated between the crown-shaped component 81 and the widened base 73 of the fixed hollow component 72. The particles of active principle are accommodated in these orifices 75a, 75b between the piston 76 and a porous membrane which is flush with the outer lateral surface of the hollow component 72.

Advantageously, a transverse secondary protective seal is arranged at that end of the ejection tube 54 which adjoins the convergent part of the central channel of the hollow cylindrical component 72.

This second version of the first preferred embodiment of the syringe functions as follows.

The step leading to the firing of the pyrotechnic charge 55 by the user is strictly identical to that described above for the first preferred embodiment of the invention. The gases then emitted by the combustion of the pyrotechnic charge 55 first invade the chamber 53 and then the ducts 67a, 67b so as to occupy the free space 82 situated between the hollow cylindrical component 72 and said hollow body 71. The gases accumulating in this space 82 thus exert pressure on the porous wall which obturates the orifices 75a, 75b accommodating the particles of active principle. In a second step, the piston 76 is displaced in the central channel until, on the one hand, its six openings 78 come into line with the six orifices 75a, 75b containing the particles, in such a way as to release the particles into said piston 76, and, on the other hand, until its orifices 77 situated in its upstream zone come into line with the orifices 74 of the upstream part of the hollow cylindrical component 72, in order to allow the gases to invade the upstream part of the internal channel of the piston 76, said upstream part being delimited by the protective seal 79. The piston 76 reaches the end of its travel by coming into abutment against an internal shoulder of the central channel of the hollow cylindrical component 72. Chronologically, upon displacement of said piston 76, the phase in which the openings 78 come into line with the orifices 75a, 75b containing the particles occurs just before the phase in which the other orifices 74, 77 come into line, in such a way that the particles have already begun to be released just before the rise in pressure in the upstream part of the internal channel of the piston 76. Once the pressure has reached a threshold value in said upstream part of the piston 76, the protective seal 79 opens out like petals, without fragmenting, and generates a shock wave which entrains the particles of active principle, first into the ejection tube 54, then toward the skin of the patient who is to be treated. The secondary protective seal, advantageously positioned at the start of the ejection tube 54, serves to temporarily retain, in the syringe 50, those particles which have been blown from their orifices 75a, 75b, said protective seal having no kind of resistance to the shock wave emitted upstream and likewise opening out like petals.

Figure 7:
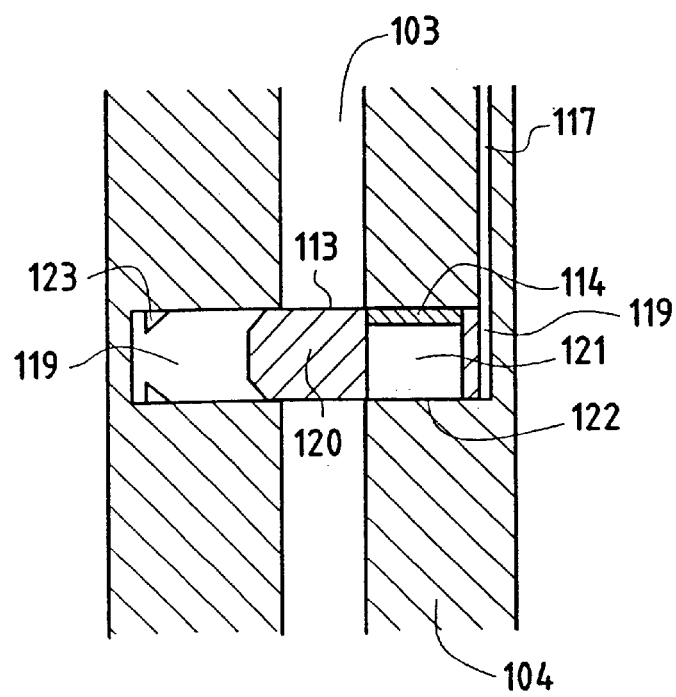
FIG. 7 is a diagram, in longitudinal cross section, of the system for retention of the particles in the syringe in FIGS. 5 and 6.

Referring to FIGS. 5, 6 and 7, a needleless syringe 100 according to the second preferred embodiment of the invention comprises, in succession, a pyrotechnic gas generator 102, an expansion chamber 103, a system for retention of the particles, and a tube 104 used for ejection of said particles and intended to bear against the skin of the patient who is to be treated. The pyrotechnic gas generator 102, of which only the contour and the pyrotechnic charge 105 have been shown in FIGS. 5 and 6 and which functions on the basis of a percussion device, a pyrotechnic charge 105 and a primer, is identical in every point to that described above for the first preferred embodiment of the invention. The pyrotechnic charge 105 has a plane annular face opening out onto the expansion chamber 103. The expansion chamber 103 and the ejection tube 104 have the same diameter, and their boundary is marked by a substantially cylindrical transverse channel 119, one end of which is plane and closed, and the other end of which, also plane, continues via a duct 117 which opens into said chamber 103, in a zone very close to the pyrotechnic charge 105 and just downstream of a transverse filter 130 intended to filter the solid particles and cool the gases. The transverse channel 119 is in part occupied by a piston 113 of substantially cylindrical shape which has, in continuity with one another, a solid part 120 and a hollow part 121, of identical diameter, said piston 113 being delimited, on the axis of the transverse channel 119, by two plane circular faces. The hollow part 121 of the piston 113, intended to contain the pulverulent active principle, has a substantially cylindrical shape and is delimited, on the axis of the channel 119, by a plane circular face belonging to the solid part 120 and a plane circular face representing one of the two ends of the piston 113. Moreover, this hollow part 121 has, on its lateral wall and at diametrically opposite positions in relation to the axis of said hollow part 121, a protective seal 114 which can burst at above a threshold pressure, and an opening 122 which means that said hollow part 121 can be likened to an open space.

The protective seal 114 and the opening 122 have a length, along the axis of the transverse channel 119, which is smaller than the diameter of the chamber 103 and they are aligned in such a way as to have the same axis of symmetry. The length of the hollow part 121, measured along its axis of symmetry, remains less than the thickness of the lateral wall of the syringe 100, and the total length of the piston 113, along its axis, is slightly greater than the length represented by the sum of the length of the part of the channel 119 ending in the duct 117 and of the diameter of the chamber 103. The piston 113 is driven into that part of the transverse channel 119 ending in the duct 117 in such a way that, on the one hand, its solid part 120 perfectly isolates the chamber 103 from the ejection tube 104, extending beyond either side of said chamber 103 or said tube 104, and, on the other hand, its hollow part 121 is included integrally in the part of the channel 119 terminating in the duct 117. The piston 113 is mounted so as to slide by force in the channel 119, so that the outer lateral wall of said piston 113 is in contact with the inner wall of said channel 119. In this way, the hollow part 121 of the piston 113 is closed, since the inner wall of the channel 119 closes the opening 122. The piston 113 occupies the channel 119 in a position such that, if it were translated in said channel 119 until its hollow part 121 was in continuity with the chamber 103 and the ejection tube 104, without undergoing other movements, the protective seal 114 and the opening 122 would be perpendicular to the axis of the chamber 103 and of the tube 104, and the protective seal 114 would be upstream of the opening 122 with respect to the direction of propagation of the gases originating from the pyrotechnic charge 105. A free space remains between the piston 113 and the bottom of the part of the channel 119 in which it is driven, said space communicating with the duct 117. The unoccupied part of the channel 119, ending in a plane and closed end, has a narrowing 123 in proximity to said end. Finally, the ejection tube 104 can also end in a shock-absorbing rim in order to facilitate the contact of the syringe 100 on the patient's skin.

This second preferred embodiment of the invention functions as follows. The step leading to the firing of the pyrotechnic charge 105 by the user is identical to that described above for the first preferred embodiment of the invention. The gases then emitted by the combustion of the pyrotechnic charge 105 simultaneously invade the chamber 103, delimited by the solid part 120 of the piston 113, and the duct 117. The gases surge into the free space situated between said piston 113 and the plane end of the part of the channel 119 in which it is driven. Referring to FIG. 6, this space expands under the effect of the pressure, displacing the piston 113 which is then locked in the narrowing 123 of the channel 119. In this end position, the piston 113 thus aligns its hollow part 121 with the chamber 103 and the tube 104. At the start of its displacement, the piston 113 had already begun to open its hollow part 121 since the inner wall of the channel 119 no longer completely obturated said hollow part 121, thereby releasing the solid particles of active principle into the ejection tube 104. Once locked by the narrowing 123, the piston 113 continues momentarily to obturate the chamber 103 whose pressure level increases. Once this pressure level has reached a threshold level, the protective seal 114 yields, creating a shock wave which picks up and accelerates the particles still in the form of a diffuse cloud. The release of the particles into the tube 104 and the rupture of the protective seal 114 must take place over a very short interval of time, of the order of a few milliseconds, in order to ensure that the particles have not had time to regroup.

What is claimed is:

1. A needleless syringe (1, 50, 100) comprising a trigger, a gas generator continued by a gas expansion chamber (3, 53, 103), a piston (13, 76, 113), an ejection tube (4, 54, 104), said particles being housed outside said tube (4, 54, 104), and the gases, emitted by said generator, bringing about the entry of the particles into the tube (4, 54, 104) by displacement of said piston (13, 76, 113), then their acceleration in said tube (4, 54, 104), characterized in that the piston (13, 76, 113) has a protective seal (14, 79, 114) which is calibrated in such a way that said protective seal (14, 79, 114) is situated upstream of the particles released into the tube (4, 54, 104) and, by yielding at above a threshold pressure, contributes to creating a shock wave intended to entrain said particles.

2. The needleless syringe as claimed in claim 1, characterized in that the gas generator is a pyrotechnic generator (2, 52, 102) comprising a pyrotechnic charge (5, 55, 105) and an initiation device.

3. The needleless syringe as claimed in claim 1, characterized in that the particles are situated in at least one fixed seat (18, 75*a*, 75*b*) outside the conduit of the tube (4, 54), each seat (18, 75*a*, 75*b*) being obturated by the piston (13, 76) positioned in said tube (4, 54), said piston (13, 76) being displaceable, under the effect of the gases, in order to open each seat (18, 75a, 75b) and release the particles into the tube (4, 54).

4. The needleless syringe as claimed in claim 3, characterized in that a propulsion device allows the particles released by the piston (13, 76) to be thrust into the tube (4, 54) from their seat (18, 75a, 75b).

5. The needleless syringe as claimed in claim 4, characterized in that the propulsion device is established by conveying gas via at least one duct (17a, 17b, 67a, 67b) connecting that zone of the chamber (3, 53) situated near the gas generator to the seats (18, 75a, 75b) for the particles.

6. The needleless syringe as claimed in claim 5, characterized in that the particles are housed in the end part of each duct (17a, 17b, 67a, 67b), against the piston (13, 76).

7. The needleless syringe as claimed in claim 3, characterized in that the piston (13, 76) is formed by a hollow cylindrical body whose side wall has at least one opening (15a, 15b, 78).

8. The needleless syringe as claimed in claim 7, characterized in that the tube (4, 54) has a device for arresting and positioning the piston (13, 76) situated between said piston (13, 76) and that end of the tube (4, 54) through which the particles are ejected, each opening (15a, 15b, 78) on the side wall of the piston (13, 76) corresponding with each seat (18, 75a, 75b) for the particles.

9. The needleless syringe as claimed in claim 8, characterized in that the piston (13, 76) is positioned in the tube in such a way that the protective seal (14, 79) is situated upstream of the openings (15a, 15b, 78) and said protective seal (14, 79) is calibrated so as to yield at a threshold pressure reached by the gases when the piston (13, 76) is arrested by the limit stop device.

10. The needleless syringe as claimed in claim 1, characterized in that the tube (104) has a transverse channel (119) in which is housed the piston (113) which has a solid part (120) and a hollow part (121) containing the particles, and said piston (113), which is housed in the transverse channel (119) so as to initially obturate the tube (104) with its solid part (120), can be displaced along the transverse channel (119), by virtue of a thrust device, until its hollow part (121) is positioned in the continuation of the tube (104).

11. The needleless syringe as claimed in claim 10, characterized in that the thrust device is established by conveying gas via a duct (117) connecting that zone of the chamber (103) situated near the gas generator to the transverse channel (119).

12. The needleless syringe as claimed in claim 10, characterized in that the transverse channel (119) has a locking means (123) for holding the piston (113) in a position in which its hollow part (121) is situated in the continuity of the tube (104).

13. The needleless syringe as claimed in claim 10, characterized in that the hollow part (121) of the piston (113) containing the particles is initially closed by the wall of the transverse channel (119).

14. The needleless syringe as claimed in claim 10, characterized in that the protective seal is situated in the area of the hollow part (121) of the piston (113) so that, on being displaced, the piston (113) opens its hollow part (121) in such a way as to bring the particles into the tube (104), and the protective seal (114) is intended to yield at above a threshold pressure in order to expel the particles.

15. The needleless syringe as claimed in claim 10, characterized in that the thrust device is formed by a spring.

16. The needleless syringe as claimed in claim 13, characterized in that the protective seal is situated in the area of the hollow part (121) of the piston (113) so that, on being displaced, the piston (113) opens its hollow part (121) in such a way as to bring the particles into the tube (104), and the protective seal (114) is intended to yield at above a threshold pressure in order to expel the particles.

\* \* \* \* \*